United States Patent [19]

Paust et al.

[11] Patent Number: 4,503,238

[45] Date of Patent: Mar. 5, 1985

[54] PREPARATION OF DIHYDRO-4,4-DIMETHYLFURAN-2,3-DIONE

[75] Inventors: Joachim Paust, Neuhofen; Hartmut Leininger, Neustadt, both of Fed. Rep. of Germany

[73] Assignee: BASF Aktiengesellschaft, Fed. Rep. of Germany

[21] Appl. No.: 552,389

[22] Filed: Nov. 16, 1983

[30] Foreign Application Priority Data

Nov. 18, 1982 [DE] Fed. Rep. of Germany ....... 3242560

[51] Int. Cl.³ .......................................... C07D 307/60
[52] U.S. Cl. .................................................... 549/319
[58] Field of Search ......................................... 549/319

[56] References Cited

U.S. PATENT DOCUMENTS 4,225,506  9/1980  Schmid ................................ 549/319

FOREIGN PATENT DOCUMENTS 0006156  1/1980  Fed. Rep. of Germany .

OTHER PUBLICATIONS

C.A. 92, No. 5,-2/4/80, p. 765, No. 41738q.
Houben-Weyl, "Methoden der Organischen Chemie", vol. IV/1a, (1981), p. 512.

Primary Examiner—Norma S. Milestone
Attorney, Agent, or Firm—Keil & Weinkauf

[57] ABSTRACT

Dihydro-4,4-dimethylfuran-2,3-dione is prepared by oxidation of racemic dihydro-3-hydroxy-4,4-dimethyl-2(3H)-furanone by a process in which the oxidation is carried out by gradually adding powdered calcium oxide to a solution of racemic dihydro-3-hydroxy-4,4-dimethyl-2(3H)-furanone and chlorine in the inert organic solvent.

6 Claims, No Drawings

PREPARATION OF DIHYDRO-4,4-DIMETHYLFURAN-2,3-DIONE

The invention relates to an improved process for the preparation of dihydro-4,4-dimethylfuran-2,3-dione by oxidation of pantolactone with chlorine and calcium oxide in an anhydrous medium.

Dihydro-4,4-dimethylfuran-2,3-dione, which is also known as ketopantolactone, is an important intermediate for the sythesis of optically active dihydro-3-hydroxy-4,4-dimethyl-2(3H)-furanone. This compound, which is also called pantolactone, is an important starting material for the preparation of R-(+)-pantothenic acid or R-(+)-panthenol.

European Laid-Open Application No. 0,006,156 discloses that ketopantolactone can be prepared by oxidation of racemic pantolactone, advantageously using solid calcium hypochlorite, barium hypochlorite or lithium hypochlorite in the organic phase.

However, the use of a solid hypochlorite, in particular calcium hypochlorite, as an oxidizing agent has various disadvantages on an industrial scale. For example, to prepare it for use, the oxidizing agent has to be subjected to an expensive drying procedure at from 60° to 70° C. under greatly reduced pressure for 24 hours. The oxidizing agent used contains impurities, such as calcium carbonate and sodium chloride. Furthermore, the calcium hypochlorite content, which must be known in order to be able to maintain the stoichiometry of the reaction, has to be determined specially. A further disadvantage is the relatively long reaction time. Finally, the yields of about 75% stated in the examples of European Laid-Open Application No. 0,006,156 described are not sufficient for an industrial process.

We have found that dihydro-4,4-dimethylfuran-2,3-dione is obtained in substantially higher yields than hitherto and by a substantially simpler procedure, by oxidation of dihydro-3-hydroxy-4,4-dimethyl-2(3H)-furanone in an organic solvent, if racemic R,S-pantolactone and chlorine in an organic medium are initially taken, and powdered calcium oxide is metered in continuously in the absence of water.

It is assumed that the oxidation does not take place via the stage of calcium hypochlorite, at least not via the formation of solid calcium hypochlorite or chloride of lime, since, when anhydrous calcium oxide reacts with dry chlorine in an organic solvent, the product obtained is not calcium hypochlorite or chloride of lime. Obviously, calcium hydroxide and small or large amounts of water are required for the formation of calcium hypochlorite, since the latter is obtained industrially by passing chlorine into an aqueous suspension of calcium hydroxide, followed by salting out.

It is therefore surprising that the oxidation according to the invention proceeds smoothly, and that excellent yields of above 90% can be obtained within the short reaction time of from 60 to 120 minutes under the mild reaction temperatures of from 20° to 30° C.

The reaction is carried out in an inert organic solvent, i.e. a solvent which is inert to oxidation under the reaction conditions and particularly inert to chlorine. Examples of suitable inert organic solvents are halohydrocarbons, such as methylene chloride or chloroform, aromatic hydrocarbons, such as benzene or chlorobenzene, and in particular acetonitrile.

The oxidation is advantageously carried out at from about −10° C. to about 50° C., preferably from 20° C. to 40° C. The reaction time is in general from 0.3 to 2.0, preferably from 1 to 2, hours.

We have found that, as a rule, from 1.2 to 1.6 mole equivalents of chlorine and from 2.0 to 4.0 mole equivalents of calcium oxide are required per mole equivalent of dihydro-3-hydroxy-4,4-dimethyl-2(3H)-furanone.

After filtration, the reaction mixture is worked up in a conventional manner, by distillation or by evaporation followed by crystallization.

It is particularly advantageous to recrystallize the ketopantolactone from methyl tert.-butyl ether.

EXAMPLE 1

32.5 g of racemic dihydro-3-hydroxy-4,4-dimethyl-2(3H)-furanone (R,S-pantolactone) in 300 ml of acetonitrile dried over a molecular sieve were initially taken in a four-neck flask equipped with a mechanical stirrer, a reflux condenser, an internal thermometer and a gas inlet tube.

25.0 g of chlorine gas, which had been dried by being passed through a wash bottle filled with concentrated sulfuric acid, were fed into this solution at from 0° to 10° C.

The gas inlet tube was removed, and a metering hopper for solids was then used to add 43.7 g of calcium oxide to the reaction mixture in the course of 60 minutes. By cooling with a cold bath, the internal temperature was kept at 25° C. When the addition was complete, stirring was continued for 5 minutes.

The mixture was then filtered, the residue was washed with 100 ml of acetonitrile, and the clear colorless solution was evaporated down in a rotary evaporator at room temperature under 14 mbar. 33.3 g of a colorless crystalline material of melting point 63°–65° C. were obtained. The yield of dihydro-4,4-dimethylfuran-2,3-dione was determined by gas chromatography, using an internal standard. It was 89% for 4.4% of unconverted starting material (dihydro-3-hydroxy-4,4-dimethyl-2-(3H)-furanone). This corresponds to 28.5 g of dihydro-4,4-dimethylfuran-2,3-dione.

Recrystallization from methyl tert.-butyl ether gave 24.0 g of ketopantolactone of melting point 67° to 68° C.

EXAMPLE 2

When the procedure used in Example 1 was followed, except that the reaction temperature employed was 30° C. instead of 25° C., the dihydro-4,4-dimethylfuran-2,3-dione was obtained in a yield of 91%.

EXAMPLE 3

When the procedure described in Example 1 was followed, except that the calcium oxide was added to the reaction mixture in the course of 120 minutes instead of 60 minutes, the dihydro-4,4-dimethylfuran-2,3-dione was obtained in a yield of 95%.

We claim:
1. A process for the preparation of dihydro-4,4-dimethylfuran-2,3-dione by oxidation of racemic dihydro-3-hydroxy-4,4-dimethyl-2(3H)-furanone, wherein the oxidation is carried out by gradually adding powdered calcium oxide to a solution of racemic dihydro-3-hydroxy-4,4-dimethyl-2(3H)-furanone and chlorine in an inert organic solvent.

2. A process as claimed in claim 1, wherein, based on 1 mole equivalent of dihydro-3-hydroxy-4,4-dimethyl-2(3H)-furanone, from 1.2 to 1.6 mole equivalents of chlorine are initially taken and from 2.0 to 4.0 mole equivalents of calciulm oxide are gradually added.

3. A process as claimed in claim 1, wherein the oxidation is carried out at from −10° to 50° C.

4. A process as claimed in claim 1, wherein the oxidation is carried out at from 20° to 40° C.

5. A process as claimed in claim 1, wherein the oxidation is carried out in acetonitrile.

6. A process as claimed in claim 1, wherein the crude product obtained is recrystallized from methyl tert.-butyl ether.

* * * * *